United States Patent
Allen et al.

(10) Patent No.: US 6,235,244 B1
(45) Date of Patent: May 22, 2001

(54) UNIFORMLY EXPANDABLE MULTI-CHANNEL PIPETTOR

(75) Inventors: Dave Allen, Marlborough, MA (US); Robert H. Zier, Annapolis, MD (US); George P. Kalmakis, Reading, MA (US); Victor A. Torti, Brookline; Gary E. Nelson, Hollis, both of NH (US)

(73) Assignee: Matrix Technologies Corp., Hudson, NH (US)

( * ) Notice: Subject to any disclaimer, the term of this patent is extended or adjusted under 35 U.S.C. 154(b) by 0 days.

(21) Appl. No.: 09/211,767

(22) Filed: Dec. 15, 1998

Related U.S. Application Data

(60) Provisional application No. 60/112,316, filed on Dec. 14, 1998.

(51) Int. Cl.[7] ........................................ B01L 3/02
(52) U.S. Cl. .................. 422/100; 73/864.17; 73/864.25
(58) Field of Search .................. 422/100; 73/864.17, 73/864.14, 864.25

(56) References Cited

U.S. PATENT DOCUMENTS

| 4,801,434 | 1/1989 | Kido et al. . |
|---|---|---|
| 4,824,642 | 4/1989 | Lyman et al. . |
| 4,830,832 | 5/1989 | Arpagaus et al. . |
| 5,057,281 | 10/1991 | Torti et al. . |
| 5,061,449 | 10/1991 | Torti et al. . |

FOREIGN PATENT DOCUMENTS

| 2 205 400 | 12/1988 | (GB) . |
|---|---|---|
| 62-138735 | 6/1987 | (JP) . |
| 62-191049 | 8/1987 | (JP) . |
| 63-104655 | 5/1988 | (JP) . |
| 61-50927 | 2/1989 | (JP) . |
| 64-50928 | 2/1989 | (JP) . |
| 6504453 | 10/1966 | (NL) . |
| 97/14040 | * 4/1997 | (WO) . |

* cited by examiner

Primary Examiner—Jan Ludlow
(74) Attorney, Agent, or Firm—Wolf, Grenfield & Sacks, P.C.

(57) ABSTRACT

A pipetting system having a plurality of tip fittings whose spacing can be simultaneously, quickly, and accurately adjusted so that the spacing between each adjacent tip fitting is substantially identical. The tip fittings are attached one to another by a linkage such as a pantographic linkage. The spacing is limited by an adjustable, slidable stop. Uniformly increasing and decreasing the spacing is accomplished by pulling and pushing a rod attached to one tip fitting.

16 Claims, 6 Drawing Sheets

UNIFORMLY EXPANDABLE MULTI-CHANNEL PIPETTOR

RELATED APPLICATIONS

This application claims priority under 35 U.S.C.§119 (e) to commonly-owned, co-pending U.S. provisional patent application Ser. No. 60/112,316 entitled "Uniformly Expandable Multi-channel Pipettor," filed Dec. 14, 1998 by Torti et al., which is incorporated herein by reference in its entirety.

FIELD OF THE INVENTION

This invention relates generally to liquid transfer devices used in laboratories and, more particularly, to a multi-channel pipetting device which enables the user to uniformly, rapidly and accurately adjust the spacings between pipette tips.

BACKGROUND OF THE INVENTION

Pipetting systems are used in laboratories for the transfer of relatively small quantities of liquids. The liquid is normally drawn into the tips by suction and is subsequently released into the wells of microtiter plates or other receptacles. Frequently the transfer involves patient samples which are moved from one set of spaced receptacles to another set of receptacles having a different spacing. A multi-channel pipettor capable of being simply manipulated to vary the spacing between the pipette tips is often used for this purpose. Typically, the pipettor has a tip removing assembly that, with a minimum of force, removes tips safely and efficiently regardless of the positions of the tips and their fittings on the pipettor. One shortcoming of some prior art pipettors is that the pipette tips can only be adjusted between two uniform standard spacings of the receptacles. The standard settings must be preselected prior to manufacture. An example of such a prior art structure is found in U.S. Pat. No. 5,061,449.

A second type of multi-channel pipettor, such as that shown in U.S. Pat. No. 5,057,281, allows the spacings between the tip fittings to be varied by the user. However, the spacings between each fitting must be individually set. Thus, considerable manipulation is required to move the tip fittings from one set of spacings to another and it is difficult to accurately set the tip fittings to the desired spacings.

Therefore, it is desirable to have a multi-channel pipettor in which the tip fittings may be quickly and accurately set at a variety of uniform spacings. Moreover, it is desirable to easily vary the spacings while maintaining uniform spacing between tip fittings.

SUMMARY

The foregoing drawbacks of existing pipetting systems are overcome by the pipetting system of the present invention which uniformly and accurately spaces the tip fittings within a range of spacings, while still providing for easy tip removal. Moreover, the tip fittings may be rapidly moved from one set of uniform spacings to another. In addition, a desired spacing may be readily adjustably set.

One embodiment of the invention is a multi-channel pipetting system including a housing for the pipetting system, a slotted track connected to the housing, a plurality of pipette tip fittings slidably in a line mounted on the track, and an actuator for varying the size of the spacings between adjacent tip fittings. Each of the tip fittings is coupled together by a linkage to maintain a substantially identical spacing between each adjacent pair of tip fittings, regardless of a size of the spacing between adjacent tip fittings.

Another embodiment of the invention is a multi-channel pipetting system that includes a plurality of ducts, a housing for the pipetting system, a slotted track in the housing, and a plurality of pipette tip fittings, with one tip fitting being connected to each duct. All but one tip fitting is slidably mounted on the track. A pantographic linkage is connected to each of the tip fittings. An actuating rod is attached to one end of the tip fittings for varying spacing between adjacent tip fittings.

Another embodiment of the invention is a multi-channel pipetting system that includes a plurality of ducts, a housing for the pipetting system, a slotted track in the housing, and a plurality of pipette tip fittings. One tip fitting is connected to each duct. All but one tip fitting is slidably mounted on the track. The system also includes means interconnecting the tip fittings to form an array and enabling all but one tip fitting on the plate to move relative to the other tip fittings thereon. The spacing between adjacent tip fittings is substantially identical regardless of the size of the spacing. An actuating rod is attached to one of the tip fittings for varying the spacing between adjacent tip fittings.

BRIEF DESCRIPTION OF THE DRAWINGS

The objects, advantages and features of this invention will be more clearly appreciated from the following detailed description when taken in conjunction with the accompanying drawings in which.

DETAILED DESCRIPTION

Figure 1:
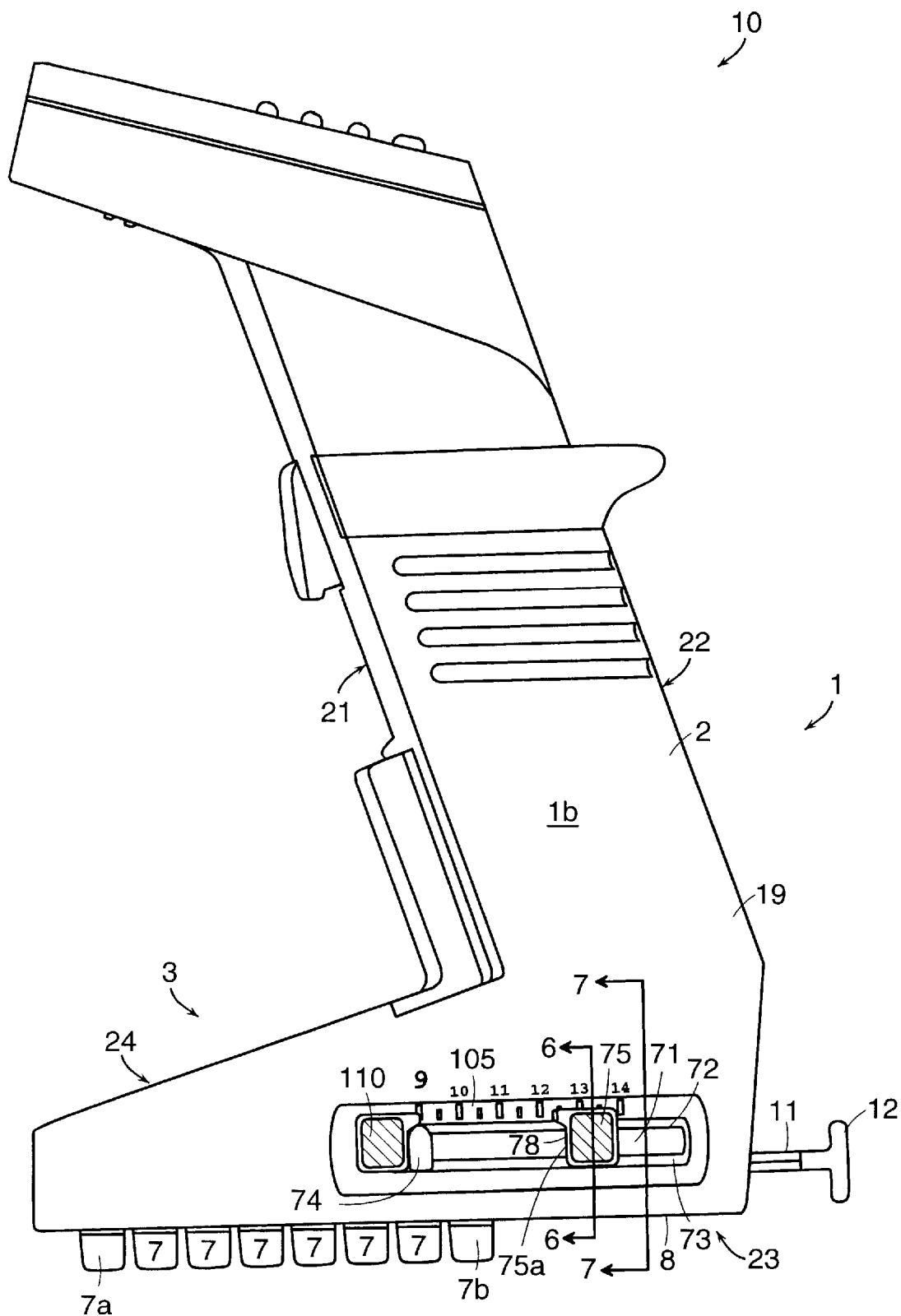
FIG. 1 is a side elevational view of the multi-channel pipettor of this invention.
Figure 2:
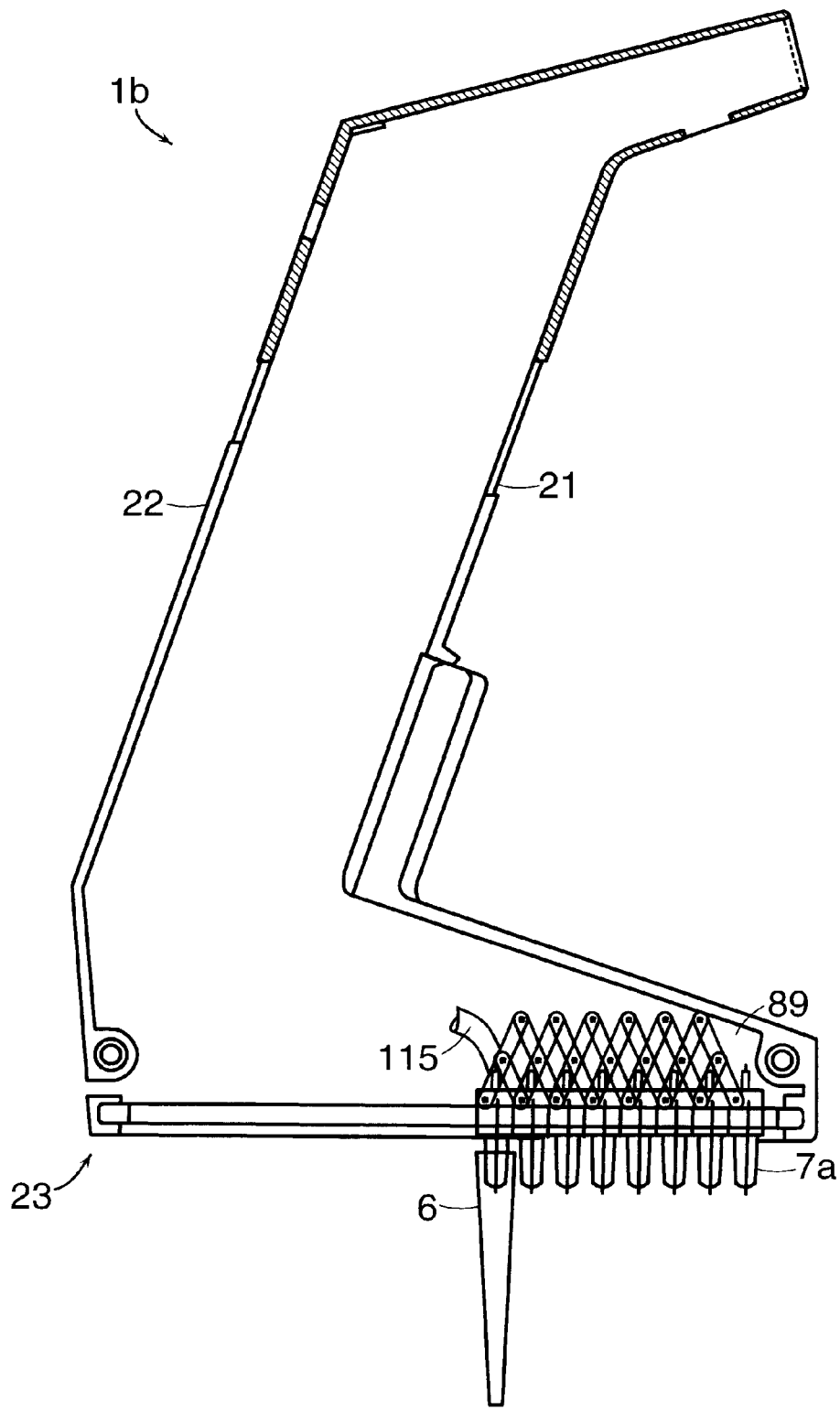
FIG. 2 is a cross-sectional side view of the multi-channel pipettor of FIG. 1 showing the pipettor tips and tip fittings in a closely spaced position.
Figure 3:
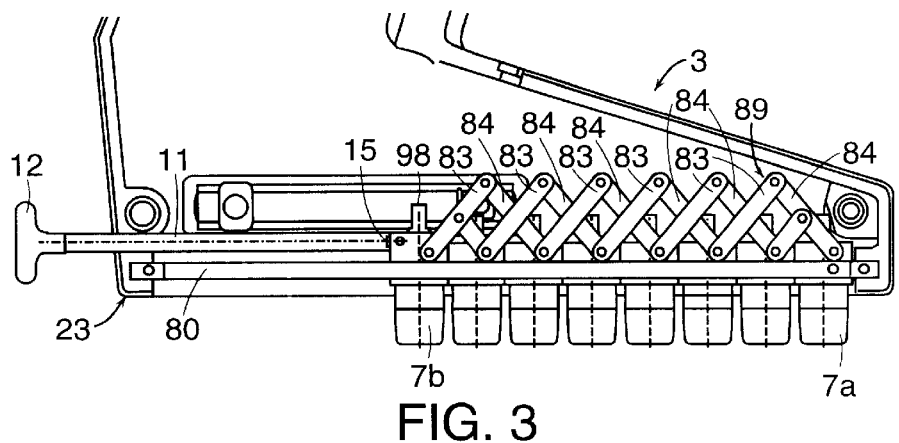
FIG. 3 is a partial cross-sectional view of the pipettor of FIG. 2 showing the tip fittings and tips in the position of FIG. 2.

With reference now to the drawings, and more particularly to FIGS. 1–3, the pipettor 10 of the present invention will now be described. The pipettor 10 of this invention has a boot-shaped housing 1 as shown in FIG. 1 that includes a handle section 2 and a lower section 3, having a bottom section 8, from which a plurality of tip fittings 7 project downwardly. In the embodiment shown, eight tip fittings are included, but it should be appreciated that the number may vary, depending upon a user's needs.

The housing 1 of the pipetting system typically is formed of a pair of mating half shells 1a (not illustrated) and 1b. The shells 1a and 1b include sidewalls 19 and 20 (not illustrated) and front and back walls 21 and 22 that together define the handle section 2 and the lower section 3. The front, back and bottom of the lower section 3 are enclosed by the walls 21, 22 and 23, while the top of the bottom section forward of the handle is enclosed by wall 24.

Figure 6:
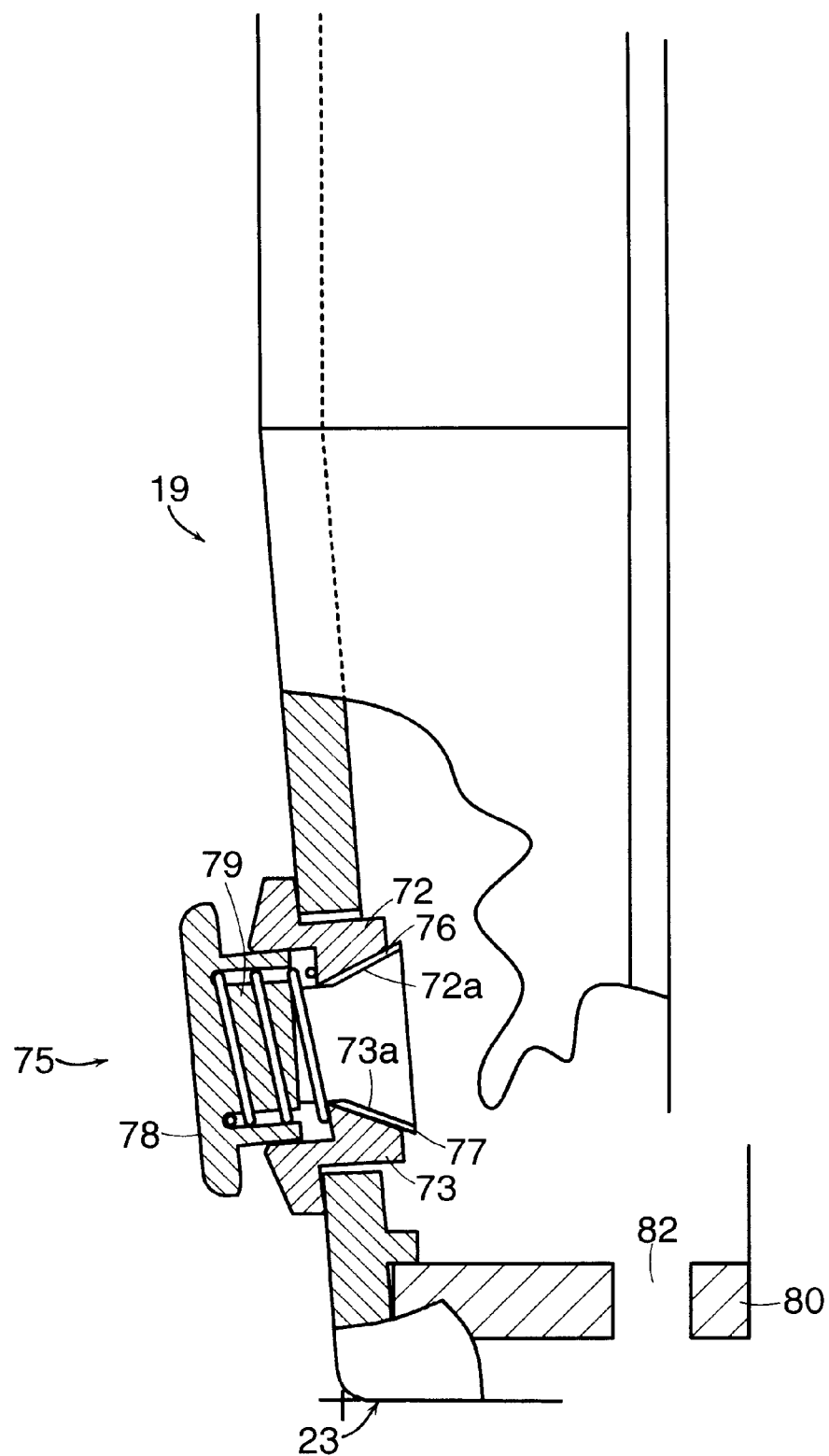
FIG. 6 is a cross-sectional view of the pipettor taken along the section line 6—6 in FIG. 1.
Figure 7:
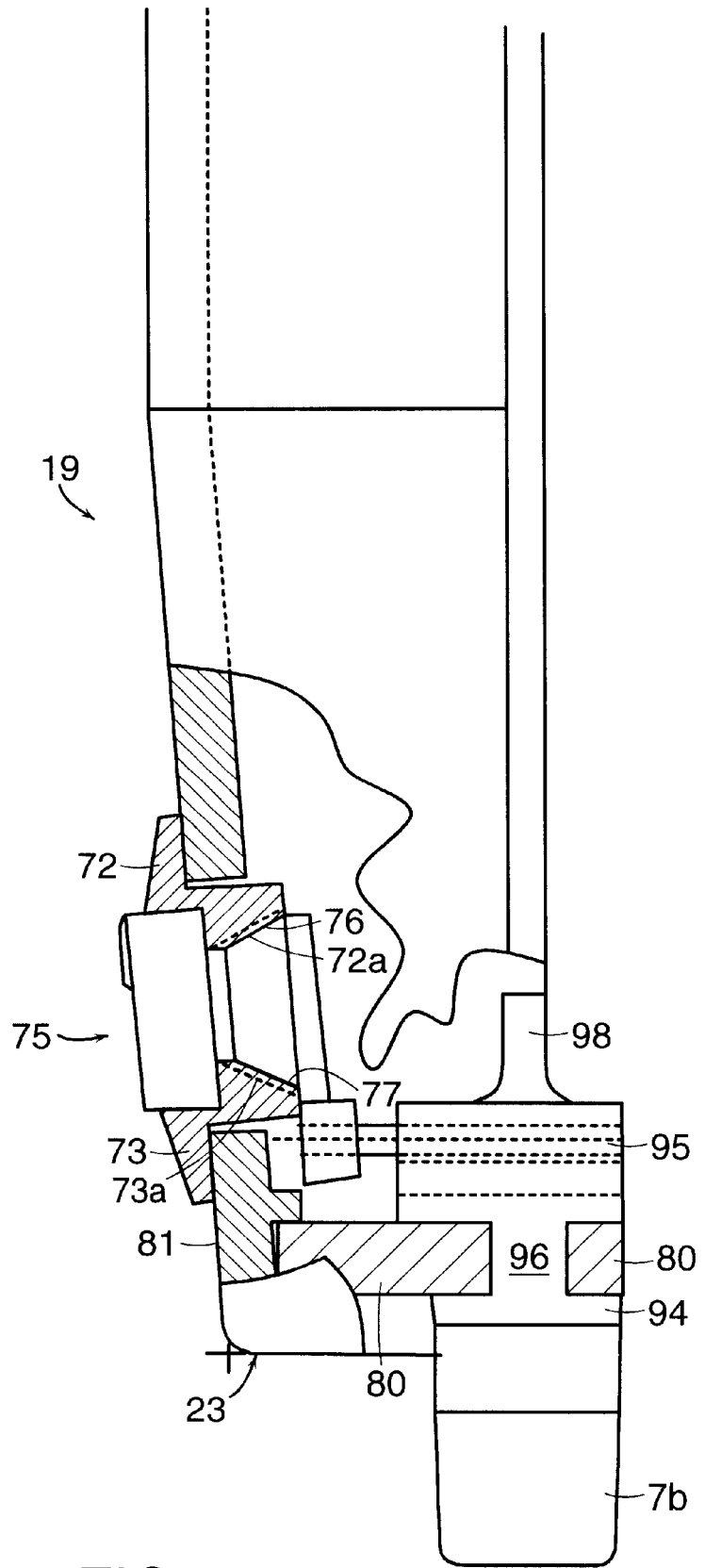
FIG. 7 is a cross-sectional view of the pipettor taken along the section line 7—7 in FIG. 1.
Figure 8:
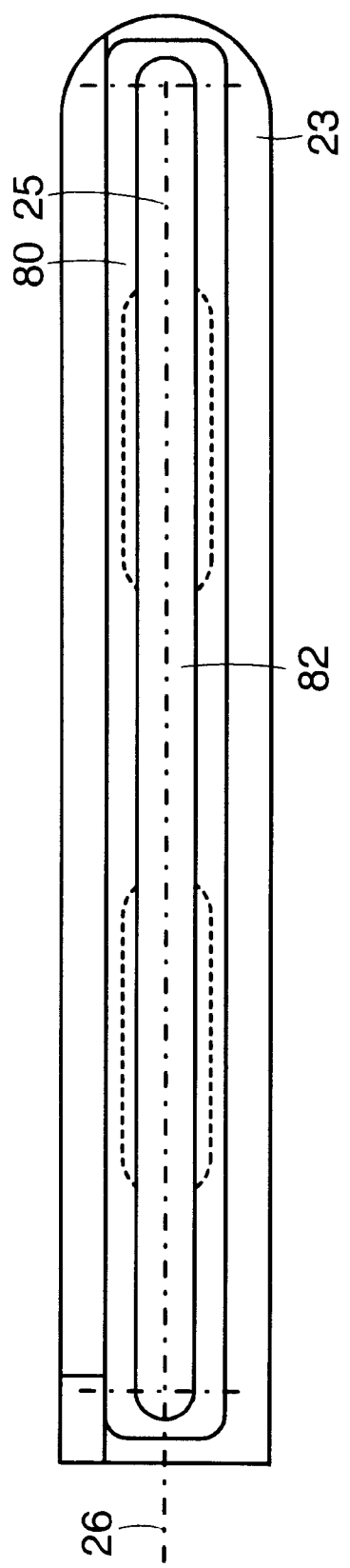
FIG. 8 is a bottom plan view of the pipettor of FIG. 1 in which the tip fittings are not shown.

As shown in FIG. 8, all but one (fitting 7a) of the tip fittings 7 slide along an elongated aperture 25 provided in the bottom wall 23. The aperture 25 extends substantially the full length thereof symmetrical with respect to the parting line 26 that joins the two shells. FIGS. 6 and 7 show a tip fitting mounting plate 80, which is secured immediately above the bottom wall 23 of the housing by slots 81 formed in each half shell 1a and 1b. The tip fitting mounting plate 80 includes an elongated slotted track 82. The elongated slotted track 82 is narrower and somewhat shorter than the aperture 25 in the bottom wall 23.

As shown in FIG. 7, each of the tip fittings disposed in the elongated slotted track 82 includes a stem 94. The width of stem 94 at its upper end is larger than the width of the elongated slotted track 82. Consequently, the edges of the stem 94 bear against the lower surface of the mounting plate 80. Above the stem 94 each tip fitting has a waist 96 which rides along the elongated slotted track 82. Each tip fitting has a shoulder 95 above the waist 96. The shoulder 95 has a width greater than the elongated slotted track 82, which forms a track along which all the tip fittings 7 are slidably disposed, and which guides tip fittings 7. Tip fitting 7a is fixed with respect to the track and does not move. Therefore, with the exception of tip fitting 7a, the tip fittings may be moved toward and away from the front wall 21.

Referring now to FIG. 2, pipette tips 6 are attachable to the tip fittings 7. Those of ordinary skill in the art will recognize that many types of pipette tips are available which may be used interchangeably provided that they are compatible with the size of the tip fittings 7. The upper end of each tip fitting carries a nipple 98 which in turn is connected to a duct 115, only an exemplary one of which is shown. A passage extends through each tip fitting from the lower end of the stem 94 to the upper end of nipple 98, which passage is in fluid communication with each duct 115. The pipetting system 10 includes a means for drawing liquid in metered volumes into the tips 6 and for expelling the liquid from the tips. This feature is not part of the present invention, and is well known to one of ordinary skill. This feature is described in U.S. Pat. No. 5,061,449, assigned to the assignee of the present application and specifically incorporated herein by reference.

The tip fittings 7 are connected together by a linkage that maintains a substantially identical, uniform spacing between each of the tip fittings, regardless of the position of the tip fittings. In a preferred embodiment shown in FIGS. 2–5, a pantographic linkage 89 is used. As shown in FIG. 3, the pantographic linkage of the preferred embodiment includes intersecting first links 83 and second links 84. A first, lower end of each first link 83 is pivotably mounted to an associated tip fitting 7. An upper, second end of each second link 84 is pivotably mounted to an upper second end of an immediately adjacent first link 83. A second, lower end of each second link is pivotably mounted to an immediately adjacent tip fitting 7. Associated first links 83 and second links 84 are pivotally coupled at their respective centers.

Figure 4:
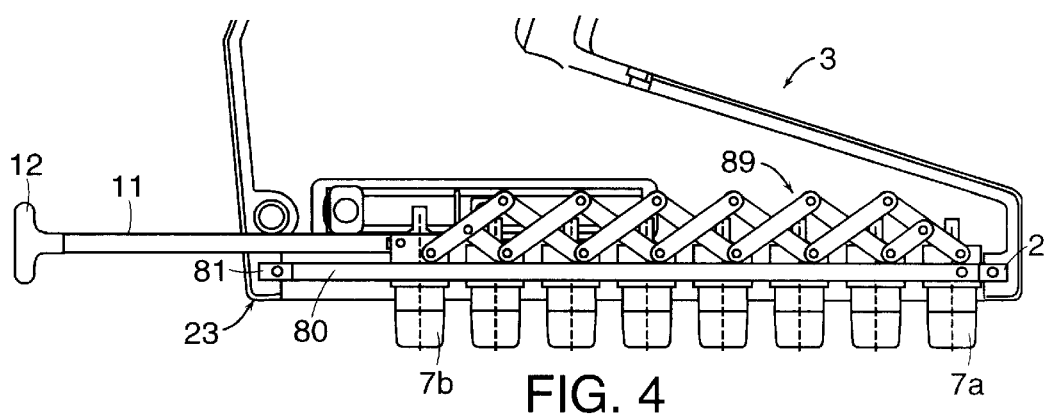
FIG. 4 is a partial cross-sectional view of the pipettor of FIG. 2 showing the tip fittings and tips in an intermediate spaced position.
Figure 5:
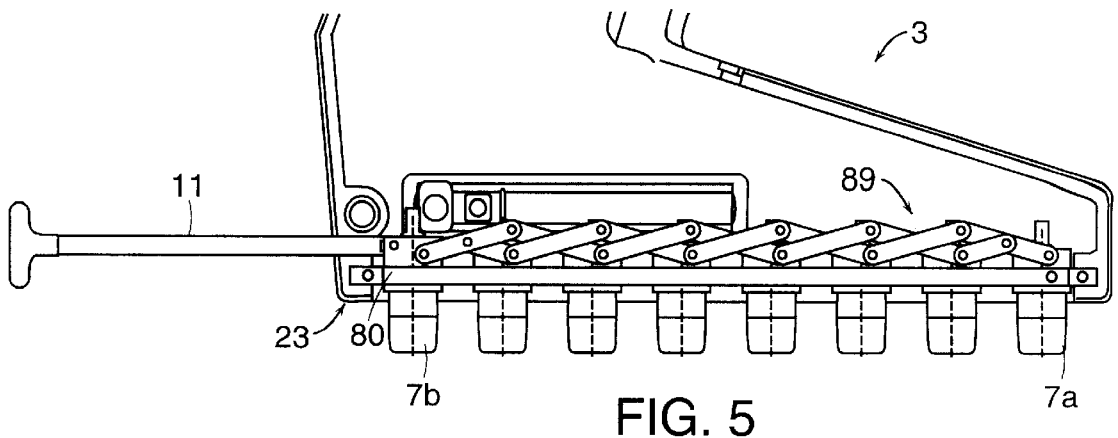
FIG. 5 is a partial cross-sectional view of the pipettor of FIG. 2 showing the tip fittings and tips with the maximum spacing.

An actuating rod 11 carrying a knob 12 on its distal end projects rearwardly away from the lower section 3 and is secured at its proximal end 15 within the housing 1 to the rear-most tip fitting 7b. By manually pushing and pulling the knob 12 and rod 11, the tip fittings are quickly and accurately moved to the desired spacings between uniformly spaced minimum and maximum positions. FIG. 3 shows the tip fittings with the minimum spacing. FIG. 4 shows an intermediate spacing, while FIG. 5 shows the linkage 89 fully extended so that the tip fittings 7 are at their maximum spacing.

As shown in FIG. 1, side wall 19 has an elongated opening 71. Referring now to FIGS. 1 and 6, upper and lower rails 72 and 73 are disposed parallel to and on either side of opening 71. The rails 72 and 73 extend along the direction of travel of the tip fittings. The rails include respective opposed surfaces 72a and 73a that form an acute angle with respect to plate 80 and that are angled with respect to one another such that the surfaces 72a and 73a of respective rails 72 and 73 are closer together facing side wall 19 than facing inwardly away from side wall 19 and toward side wall 20. The surfaces 72a and 73a of respective rails 72 and 73 are friction surfaces and contain serrations or ridges or are otherwise roughened as shown in FIGS. 6 and 7. A finger actuated stop 75 such as a button having a finger engageable surface 78 is also slidably engaged with the rails. The stop 75 has serrated, ridged or roughened friction surfaces 76 and 77 disposed parallel to respective surfaces 72a and 73a of respective rails 72 and 73, and which are urged into positive engagement with the rails 72 and 73 by biasing spring 79, as shown in FIG. 6. Spring 79 bears against rails 72 and 73 and pushes stop 75 outwardly. Applying finger pressure to the stop 75 toward wall 19 compresses the spring and releases the surfaces 76 and 77 from engagement with surfaces 72a and 73a of respective rails 72 and 73. The stop is then movable along rails 72 and 73 and within opening As shown in FIG. 1, a second finger actuated stop 110 may be included within the rails to limit the contraction of the pantographic linkage.

Preferably, a spacing indicator 74 is slidably engaged with the rails 72 and 73 and is connected to the rear-most tip fitting 7b. However, indicator 74 could be affixed to another tip fitting 7, if desired. Indicator 74 moves with tip fitting 7b and provides an indication of the spacing between adjacent tip fittings. Indicator 74 extends through opening 71 to be externally visible. A visual scale 105, as shown in FIG. 1, is provided along opening 71 and is calibrated to provide the spacing between each tip fitting for a particular location of indicator 74 with respect to scale 105. When the spacing indicator 74 engages a shoulder 75a or surface on the stop 75, or on stop 110 the spacing between the tip fittings is that shown on scale 105 with which indicator 74 is aligned. The spacing between the tip fittings may alternatively or additionally be positively established by notches provided in the rod 11 corresponding with a ball detent as disclosed in U.S. Pat. No. 5,061,449.

It will be appreciated that the tip fittings 7 are designed to slide in the tip fitting mounting plate 80 in response to movement of linkage 89. When linkage 89 is extended, the spacing between tip fittings 7 increases. Conversely, when linkage 89 is contracted, the spacing between tip fittings 7 decreases. Pulling the actuating rod 11 away from the housing 1 increases the spacing between tip fittings 7. Conversely, pushing the actuating rod 11 toward the housing 1 decreases the spacing between tip fittings 7.

In operation, the finger actuated stop 75 may be adjustably set with reference to the scale 105 to provide a uniform spacing between tip fittings. Stop 75 is pushed inwardly with a finger and slidably moved within the opening 71 until stop 75 is aligned with a desired reading on scale 105. Stop 75 is then released and surfaces 76 and 77 engage respective surfaces 72a and 73a to hold stop 75 in place. The user then grasps knob 12 and moves rod 11 until indicator 74 abuts shoulder 75a on stop 75, or on stop 110. At that point, tip fittings 7 are uniformly spaced apart as indicated by the reading on the scale 105 aligned with indicator 74. The pipettor is now ready for use.

Modifications and improvements will occur within the scope of this invention to those skilled in the art, and the above description is intended to be exemplary only. The scope of this invention is defined only by the following claims and their equivalents.

What is claimed is:

1. A multi-channel pipetting system, comprising:
   a housing for the pipetting system;
   a slotted track connected to the housing;
   a plurality of pipette tip fittings slidably mounted on the track;
   a linkage coupling together each of said tip fittings to maintain a substantially identical spacing between each adjacent pair of tip fittings regardless of a size of the spacing between adjacent tip fittings;
   an actuator for varying the size of the spacing between adjacent tip fittings;
   a first stop slidably mounted on the housing for limiting extension of the linkage; and
   a second stop slidably mounted on the housing for limiting contraction of the linkage.

2. The pipetting system of claim 1, wherein said linkage is a pantographic linkage.

3. The pipetting system of claim 1, wherein the first and second stops each comprise a finger engageable button and a spring for biasing the button into a non-movable position, the button being movable when depressed.

4. The pipetting system of claim 1, wherein the housing further comprises a scale which indicates the spacing between adjacent tip fittings.

5. The pipetting system of claim 1, wherein the slotted track is positioned in the housing.

6. The pipetting system of claim 1 wherein said actuator includes notches, and further comprising a detent engageable with said notches on said actuator for establishing the size of the spacing between adjacent tip fittings.

7. The pipetting system of claim 1 wherein each of said first and said second stops comprises:
   a rail;
   a button having a finger engageable surface for depression of the button and being structured to slide along said rail;
   friction surfaces disposed on an outer surface of said button;
   friction surfaces disposed on said rail; and
   a biasing member for urging the friction surfaces on said button against the friction surfaces on said rail when said button is not depressed.

8. A multi-channel pipetting system including a plurality of ducts, comprising:
   a housing for the pipetting system;
   a slotted track connected to the housing;
   a plurality of pipette tip fittings, one tip fitting being connected to each duct, all but one tip fitting being slidably mounted on the track;
   a pantographic linkage connected to each of the tip fittings;
   an actuating rod attached to one end of said tip fittings for varying spacing between adjacent tip fittings;
   a first stop slidably mounted on said housing for limiting extension of the pantographic linkage; and
   a second stop slidably mounted on said housing for limiting contraction of the pantographic linkage.

9. The pipetting system of claim 8, wherein the housing further comprises a scale which indicates the spacing between adjacent tip fittings.

10. The pipetting system of claim 8, wherein the slotted track is positioned in the housing.

11. A multi-channel pipetting system including a plurality of ducts, comprising:
    a housing for the pipetting system;
    a slotted track connected to the housing;
    a plurality of pipette tip fittings, one tip fitting being connected to each duct, all but one tip fitting being slidably mounted on the track;
    a linkage interconnecting the tip fittings to form an array and enabling all but the one tip fitting on the track to move relative to the other tip fittings;
    a spacing between adjacent tip fittings being substantially identical regardless of a size of the spacing;
    an actuating rod attached to another one of said tip fittings for varying the spacing between adjacent tip fittings; and
    at least one stop slidably mounted on said housing for limiting extension of the linkage for adjustably limiting the spacing between adjacent tip fittings, said stop comprising:
      a rail;
      a button having a finger engageable surface for depression of the button and being structured to slide along said rail;
      friction surfaces disposed on an outer surface of said button;
      friction surfaces disposed on said rail; and
      a biasing member for urging the friction surfaces on said button against the friction surfaces on said rail when said button is not depressed.

12. The pipetting system of claim 11, wherein said linkage comprises a pantographic linkage.

13. The pipetting system of claim 11, further comprising a spacing indicator.

14. The pipetting system of claim 11, further comprising a second stop slidably engageable with said housing to limit contraction of the linkage, and a spacing indicator.

15. The pipetting system of claim 11, wherein the slotted track is positioned in the housing.

16. A multi-channel pipetting system, comprising:
    a housing;
    a slotted track connecting to the housing;
    a plurality of pipette tip fittings slidably mounted on the track;
    a linkage coupling together each of said tip fittings to maintain a substantially identical spacing between each adjacent pair of tip fittings regardless of a size of the spacing between adjacent tip fittings;
    an actuator for varying the size of the spacing between adjacent tip fittings, said actuator including notches; and
    a detent engageable with said notches on said actuator for establishing the size of the spacing between adjacent tip fittings.

* * * * *